US00PP16447P3

(12) United States Plant Patent
Murakami

(10) Patent No.: US PP16,447 P3
(45) Date of Patent: Apr. 18, 2006

(54) *CALIBRACHOA* PLANT NAMED 'SUNBELHOPI'

(50) Latin Name: ***Calibrachoa* sp.**
Varietal Denomination: Sunbelhopi

(75) Inventor: Yasuyuki Murakami, Gamo-gun (JP)

(73) Assignee: Suntory Flowers Limited, Tokyo (JP)

( * ) Notice: Subject to any disclaimer, the term of this patent is extended or adjusted under 35 U.S.C. 154(b) by 138 days.

(21) Appl. No.: 10/810,334

(22) Filed: Mar. 26, 2004

(65) Prior Publication Data

US 2005/0216987 P1 Sep. 29, 2005

(51) Int. Cl.
*A01H 5/00* (2006.01)

(52) U.S. Cl. ..... Plt./263
(58) Field of Classification Search ..... Plt./263, Plt./356
See application file for complete search history.

(56) References Cited

U.S. PATENT DOCUMENTS

| | | | |
|---|---|---|---|
| PP9,754 | P | 12/1996 | Suzuki et al. |
| PP10,355 | P | 4/1998 | Murakami |
| PP11,558 | P | 10/2000 | Murakami |
| 2003/0126664 | P1 | 7/2003 | Murakami |

FOREIGN PATENT DOCUMENTS

| | | |
|---|---|---|
| JP | PBR 7232 | 6/1996 |
| JP | PBR 14309 | 3/2002 |

OTHER PUBLICATIONS

GTITM UPOVROM Citation for 'Sunbelhopi' as per CA PBR 04–4073; Feb. 27, 2004.*
Explanation of Publications of Japanese PBR Registration or Application and family documents thereof.
Suntory Flowers Ltd., "Flowers & Green, the newest catalog 2004" Published 2003, With Explanation.
Jackson & Perkins Wholesale, Inc., USA, "The 2004 Suntory Collection" Published 2003, With Explanation.
Pineae Greenhouses, Inc., USA, "Pineae Peak Performers featuring the 2004 Suntory COLLECTION" Published 2003, With Explanation.
Moerheim New Plant bv., USA, "Suntory Collection 2004" Published 2003, With Explanation.
Ramm Botanicals Pty Ltd., AU., "Colour Wave Collection 2003–4 . . . beautiful flowering plants" Published 2002, With Explanation.

* cited by examiner

*Primary Examiner*—Kent Bell
(74) *Attorney, Agent, or Firm*—Christie, Parker & Hale, LLP

(57) ABSTRACT

Disclosed herein is a new and distinct variety of *Calibrachoa* plant having a spreading growth habit. The *Calibrachoa* plant has abundant branching, and a great profusion of blooms, the whole plant remaining in bloom for a considerable period of time. The flowers are single and small, the petals having a vivid reddish purple color. The inside color of the corolla throat is vivid yellow and the outside of the corolla tube is brilliant greenish yellow with dark grayish reddish brown vein. The plant exhibits high resistance to heat, cold, rain and disease.

2 Drawing Sheets

Botanical/commercial classification: *Calibrachoa* sp./ *Calibrachoa* Plant.
Varietal denomination: cv. 'Sunbelhopi'.

BACKGROUND OF THE VARIETY

The present invention relates to a new variety of *Calibrachoa* plant, botanically known as *Calibrachoa* sp., originated from crossing of a *Calibrachoa* hybrid variety called 'P5' as the female parent and 'E10' as the male parent.

The female parent 'P5' (unpatented) used in the crossing of 'Sunbelhopi' is a strain of our breeding lines, having an outwardly spreading growth habit with abundant branching. It has small single flowers, the petals having a vivid reddish purple color.

The male parent 'E10' (unpatented) used in the crossing of 'Sunbelhopi' is a strain of our breeding lines, having a spreading growth habit with abundant branching. It has small single flowers, the petals having a light yellowish pink color.

In April 1999, crossing of 'P5' as the female parent and 'E10' as the male parent was conducted at Yokaichi-shi, Shiga-ken, Japan. Seedlings were obtained from that crossing and were grown in pots in glasshouses and were evaluated from October 1999. One seedling was selected in view of its growth habit, flower size and color in August 2000. That seedling was propagated by cutting and a trial was carried out by flower potting and bedding from April to November 2001. The botanical characteristics of that plant were then examined, using similar varieties 'Sunbelchipi' (U.S. Plant Pat. No. 10,355) and 'Sunbelrikupi' (U.S. Plant Pat. No. 14,729) for comparison. As a result, it was concluded that this *Calibrachoa* plant is distinguishable from any other variety, whose existence is known to us, and is uniform and stable in its characteristics. Then the new variety of *Calibrachoa* plant was named 'Sunbelhopi'.

In the following description, the color-cording is in accordance with the Horticultural Colour Chart of The Royal Horticultural Society, London, England (R.H.S. Colour Chart).

SUMMARY OF THE VARIETY

This new variety in unlike any *Calibrachoa* commercially available as evidenced by the following unique combinations of characteristics.

1. Compact and spreading growth habit with abundant branching.
2. Having a great profusion of blooms with the entire plant remaining in bloom for a considerable period of time.
3. The flowers are single and small. The petal color is vivid reddish purple (near R.H.S. N74A).
4. The plant has a high resistance to rain, cold, heat and disease.

The new variety 'Sunbelhopi' differs from the similar variety 'Sunbelchipi' in the following points.

1. The flower diameter of 'Sunbelhopi' is larger than that of 'Sunbelchipi'.
2. The petal color of 'Sunbelhopi' is vivid reddish purple (near R.H.S. N74A) where that of 'Sunbelchipi' is vivid purplish red (near R.H.S. N57A).
3. The apex shape of petal of 'Sunbelhopi' is rounded while that of 'Sunbelchipi' is obtuse.

The new variety 'Sunbelhopi' differs from the similar variety 'Sunbelrikupi' in the following points.

1. The growth habit of 'Sunbelhopi' is spreading while that of 'Sunbelrikupi' is decumbent.
2. The plant height of 'Sunbelhopi' is higher than that of 'Sunbelrikupi'.
3. The leaf of 'Sunbelhopi' is longer than that of 'Sunbelrikupi'.
4. The apex shape of petal of 'Sunbelhopi' is rounded while that of 'Sunbelrikupi' is obtuse.

The new variety of *Calibrachoa* plant 'Sunbelhopi' was asexually reproduced by the use of cuttings at Yokaichi-shi, Shiga-ken, Japan, and the homogeneity and stability thereof were confirmed. The instant plant retains its distinctive characteristics and reproduces true to type in successive generations.

BRIEF DESCRIPTION OF THE PHOTOGRAPH

The depicted plants had been reproduced by the use of cuttings and were photographed during August 2001 while growing outdoors in 18 cm pots at an age of approximately 7 months at Yokaichi-shi, Shiga, Japan.

DESCRIPTION OF VARIETY

Figure 1:
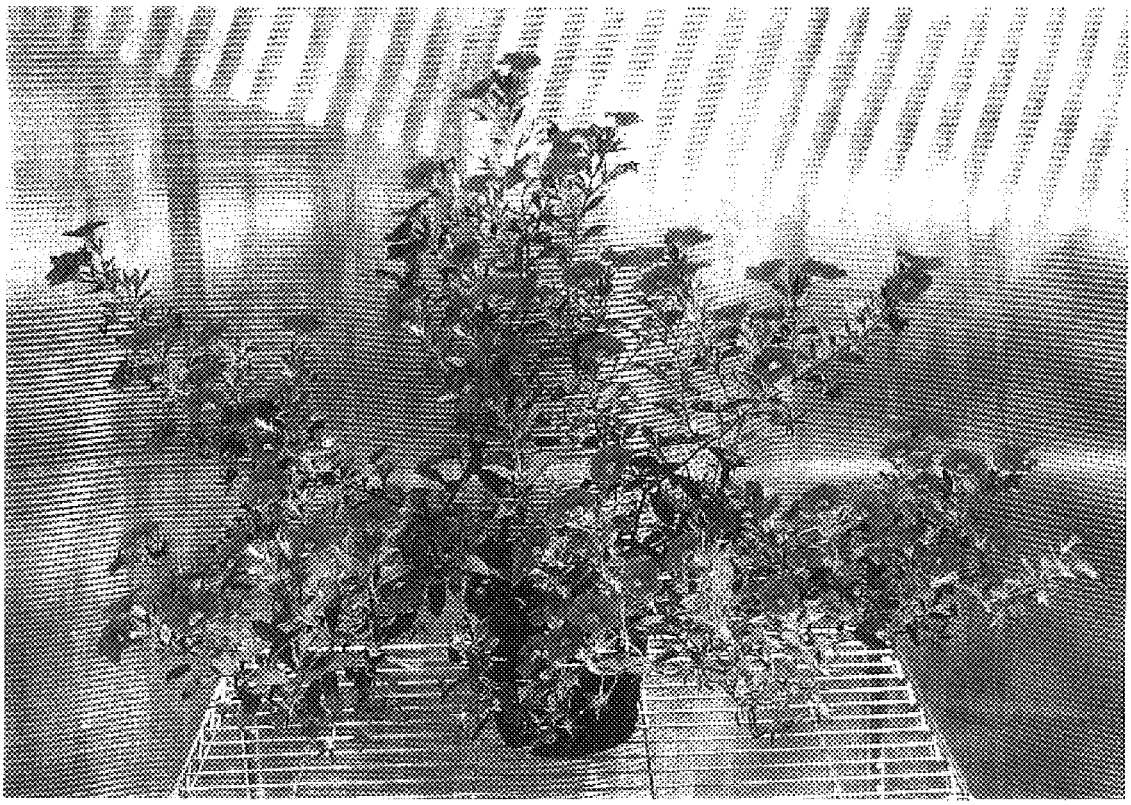
FIG. 1 illustrates a typical plant of the new variety of *Calibrachoa* plant 'Sunbelhopi' growing in a pot.
Figure 2:
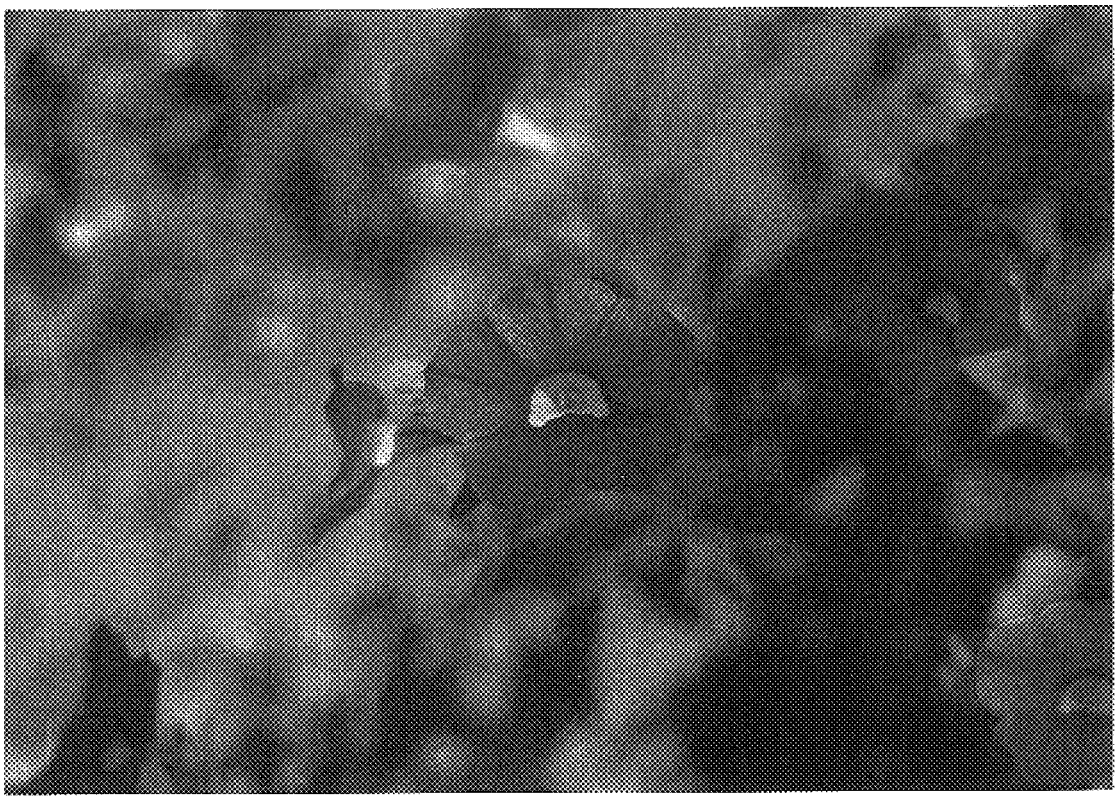
FIG. 2 is a close view of typical blossoms of the new variety of *Calibrachoa* plant 'Sunbelhopi'.

The botanical characteristics of the new and distinct variety of *Calibrachoa* plant named 'Sunbelhopi' are as follows when observed during December at Yokaichi-shi, Shiga-ken, Japan, at an age of approximately 11 months.

Plant:

*Growth habit.*—Spreading.
*Plant height.*—Approximately 25.5 cm.
*Spreading area of plant.*—Approximately 40.5 cm.
*Blooming period.*—April to late October in the southern Kanto area, Japan. The plant shape does not change throughout this period.

Stem:

*Length.*—Approximately 13.7 cm.
*Thickness.*—Approximately 2.0 mm.
*Pubescence.*—Normal.
*Branching.*—Abundant branching, especially secondary branches.
*Internode length.*—Approximately 1.3 cm.
*Color.*—Near R.H.S. 177B (grayish reddish brown).

Leaf:

*Whole shape.*—Elliptic. The apex shape is acute, and the base shape is attenuate.
*Length.*—Approximately 4.8 cm.
*Width.*—Approximately 1.6 cm.
*Color.*—Upper side color is near R.H.S. 144A (strong yellow green), lower side color is near R.H.S. 146B (moderate yellow green).
*Thickness.*—Approximately 0.3 mm.
*Pubescence.*—Sparse.

Flower:

*Facing direction.*—Slanted upward.
*Type.*—Single.
*Shape.*—Funnel-shaped, with five-fissures.
*Shape of petal tip.*—Rounded.
*Lobation.*—Shallow.
*Waviness of petal.*—Weak.
*Diameter.*—Approximately 4.0 cm.
*Depth.*—Approximately 2.5 cm.
*Tube length.*—Approximately 2.0 cm.
*Throat diameter.*—Distal end — approximately 1.0 cm.
*Tube diameter.*—Proximal end — approximately 2.0 mm.
*Color.*—Petal; near R.H.S. N74A (vivid reddish purple). Inside color of the corolla tube is near R.H.S. 9A (vivid yellow). Outside color of the corolla throat is near R.H.S. 5C (brilliant greenish yellow) with venation near R.H.S. 200B (dark grayish reddish brown).

Petals:

*Width.*—Approximately 1.7 cm.
*Length from throat.*—Approximately 1.2 cm.
*Shape.*—Very broadly obovate.
*Margin.*—Entire.
*Texture.*—Smooth.
*Color.*—Lower surface, near R.H.S. N74B with near R.H.S. N77A venation.

Buds:

*Shape.*—Cylindrical.
*Length.*—Approximately 2.0 cm.
*Diameter.*—Approximately 5.0 mm.
*Color.*—Towards apex, Near R.H.S. 70B; base, near R.H.S. 145C; Venation, near R.H.S. N77A.
*Reproductive organs.*—1 normal pistil and 5 normal stamens. The stigma is club-shaped and near R.H.S. N144D (light yellow green) in coloration. The style is approximately 4.7 mm in length and near R.H.S. 145B (brilliant yellow green) in coloration. The ovary is near R.H.S. N144D (light yellow green) in coloration. The stamens commonly are of variable length from approximately 4.7 to 7.4 mm. Pollen is formed in a quantity that is typical of *Calibrachoa* and is near R.H.S.21A (vivid orange yellow) in coloration.
*Fertility.*—Fertile, but self-incompatible.
*Peduncle.*—Approximately 0.6 mm in diameter and approximately 1.6 cm in length. The texture is smooth.

*Color.*—Near R.H.S. 144B.

*Calyx.*—Narrow. 5 sepals in fused at the base.

Sepals:

*Shape.*—Narrow elliptic.

*Apex shape.*—Obtuse.

*Base.*—Fused.

*Margin.*—Entire.

*Length.*—Approximately 1.8 cm.

*Width.*—Approximately 3.5 mm.

*Color.*—Upper surface — near R.H.S. 137B; lower surface — near R.H.S. 137C.

*Seeds.*—Near R.H.S. N186A (strong red) in coloration, approximately 0.6 mm in diameter, and generally round. The quantity is typical of *Calibrachoa.*

Physiological and ecological characteristics: High resistance to cold, heat, rain and disease, such as Powdery mildew. The resistance to heat and rain is very strong.

This new variety of *Calibrachoa* plant is most suitable for flower bedding and potting, particularly in hanging pots or planters. Pinching of old blossoms will enhance the formation of new blossoms.

It is claimed:

1. A new and distinct variety of *Calibrachoa* plant named 'Sunbelhopi', substantially as herein illustrated and described.

* * * * *